United States Patent
Baer-Beck et al.

(10) Patent No.: US 11,301,998 B2
(45) Date of Patent: Apr. 12, 2022

(54) METHOD AND SYSTEM FOR CALCULATING AN OUTPUT FROM A TOMOGRAPHIC SCROLLABLE IMAGE STACK

(71) Applicant: Siemens Healthcare GmbH, Erlangen (DE)

(72) Inventors: Matthias Baer-Beck, Erlangen (DE); Sebastian Faby, Forchheim (DE); Rainer Raupach, Heroldsbach (DE); Andre Ritter, Neunkirchen am Brand (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 125 days.

(21) Appl. No.: 16/856,121

(22) Filed: Apr. 23, 2020

(65) Prior Publication Data

US 2020/0349696 A1 Nov. 5, 2020

(30) Foreign Application Priority Data

Apr. 30, 2019 (EP) ..................................... 19171766

(51) Int. Cl.
*G06T 7/90* (2017.01)
*G06T 7/00* (2017.01)

(52) U.S. Cl.
CPC .............. *G06T 7/0012* (2013.01); *G06T 7/90* (2017.01); *G06T 2207/10081* (2013.01); *G06T 2207/30004* (2013.01)

(58) Field of Classification Search
CPC combination set(s) only.
See application file for complete search history.

(56) References Cited

U.S. PATENT DOCUMENTS

2008/0212737 A1* 9/2008 D'Souza .............. A61N 5/1049
378/65
2009/0262109 A1* 10/2009 Markowitz .......... A61B 5/0538
345/419

(Continued)

FOREIGN PATENT DOCUMENTS

WO  WO-2017091835 A2  6/2017

OTHER PUBLICATIONS

Daniel F Polan, "Tissue segmentation of computed tomography images using a Random Forest algorithm: a feasibility study", Aug. 17, 2016, Institute of Physics and Engineering in Medicine, Physics in Medicine & Biology 61( 2016), pp. 6555-6566.*

(Continued)

*Primary Examiner* — Omar S Ismail
(74) *Attorney, Agent, or Firm* — Harness, Dickey & Pierce, P.L.C.

(57) ABSTRACT

A method and a system are for calculating an output from a tomographic scrollable image stack, including a large number of generated sectional images of a tissue to be examined. In this context, a tomographic scrollable image stack is received. An output for a display is calculated. The output includes a primary image that is intended for representing the received image stack, and the output includes a secondary image with additional information. The secondary image is displayed overlaid on the primary image once an unhide signal or hide signal is received. In this context, a reference may be provided between the additional information of the secondary image and the slice of tissue for examination that is shown in the sectional image of the image stack.

26 Claims, 1 Drawing Sheet

(56) References Cited

U.S. PATENT DOCUMENTS

| | | | |
|---|---|---|---|
| 2009/0316966 A1* | 12/2009 | Marshall | A61B 6/5217 |
| | | | 382/128 |
| 2015/0140535 A1* | 5/2015 | Geri | G16H 50/50 |
| | | | 434/262 |
| 2016/0310086 A1* | 10/2016 | Besson | A61B 6/5205 |
| 2018/0338741 A1* | 11/2018 | Lyman | A61B 6/50 |
| 2020/0147412 A1* | 5/2020 | Ni | G21K 5/04 |
| 2021/0244374 A1* | 8/2021 | Zhao | A61B 6/5282 |

OTHER PUBLICATIONS

Song Hyunjoo et al: "GazeVis: Interactive 3D Gaze Visualization for Contiguous Cross-Sectional Medical Images"; IEEE Transactions on Visualization and Computer Graphics; IEEE Service Center; Los Alamitos, CA, US; vol. 20; No. 5; Mai 2014; pp. 726-739; XP011543258; ISSN: 1077-2626; DOI: 10.1109/TVCG.2013.271; 2014.

* cited by examiner

METHOD AND SYSTEM FOR CALCULATING AN OUTPUT FROM A TOMOGRAPHIC SCROLLABLE IMAGE STACK

PRIORITY STATEMENT

This application claims priority under 35 U.S.C. § 119 to European Patent Application numbers EP 19171766.9 filed on Apr. 30, 2019, the contents of which are herein incorporated by reference in their entirety.

FIELD

Embodiments of the invention generally relate to a method and system for calculating an output from a tomographic scrollable image stack.

BACKGROUND

When a tomographic scrollable image stack is displayed for medical examinations, it is frequently desirable to make additional or more detailed and/or more helpful information available to a viewer, for example a radiologist, for an examination. This additional information may be further image stacks of the same medical case with supplementary functions. For example, as well as an image stack of a computed tomography scan, a further image stack of a computed tomography scan with a contrast agent phase, and/or functional information (such as perfusion or ventilation), and/or also image stacks of the same captured data set that are reconstructed in different ways may be useful. For example, ventilation charts may be calculated. These show how well ventilated the lung is locally. These ventilation charts can be presented in different colors in accordance with the ventilation. Another category of additional information is represented by the display of annotations to the image stack.

In systems that are known in the prior art, the challenge is to present the scrollable image stacks that are provided and the additional information such that on the one hand the viewer can make the spatial correlation with the primary image information but on the other hand the primary image information—which may be relevant to the examination from the point of view of diagnostics—of the scrollable image stack is not covered up. For this purpose, in the known methods the primary image information has the additional information overlaid on it by manual selection, or is provided in a further, separate display region, as it were side by side.

The actual image stack, of the CT image for example, is represented in one picture section, and the additional information, such as the ventilation, can be represented in a further picture section next to it. For this purpose, the display regions may be represented with their picture section synchronized. These variants have the disadvantage that in each case the provision of the additional information has to be selected and deselected manually, and that in the separate representation the relationship with the respective information that is displayed is lost, since the viewer has to switch back and forth between the picture sections in order to view them. This makes correlation of the information reproduced in the two picture sections more difficult, in particular between the display positions of the information. For example, a defect may be visible in the ventilation chart, and this position has to be located in the other picture section, the actual CT image.

SUMMARY

The alternative to this way of viewing is to merge the two picture sections such that ultimately the CT image with the primary information, on the basis of which the actual diagnosis is made, is overlaid for example with the ventilation chart. However, the inventors have discovered that the additional information does not represent an actual benefit to diagnostics, and consequently the viewer has to switch the overlaying on and off manually, since the additional information only gives the viewer or the diagnostician an indication of where a region that has to be looked at in more detail is located. Thus, the inventors discovered that the actual picture section, that is needed for diagnosis, cannot be viewed in the overlaid representation. In this respect, the inventors discovered that it is necessary to switch the representation between an on and an off state, and the more detailed the picture section of the CT image and the number of additional items of information, the more complex and onerous this switching becomes.

Embodiments of the present invention provide a method and a system for calculating an output from a tomographic scrollable image stack that is provided with additional information, such that the output contains a better representation of less complexity. In particular here, the actual assessment of the picture sections, for example scrolling of the picture sections by the viewer, is to be taken into account for the calculation of an output.

According to embodiments of the invention, a method and a system are disclosed for calculating an output from a tomographic scrollable image stack.

Accordingly, and according to a first embodiment, the invention provides an in particular computer-implemented method for calculating an output from a tomographic scrollable image stack that includes a large number of generated sectional images of a tissue to be examined, comprising:

receiving a scrollable image stack from a tomography unit; and calculating the output for a display unit, wherein the output includes a primary image that is determined for representing the received image stack, and wherein the output includes a secondary image with additional information, wherein the secondary image is displayed overlaid on the primary image once an unhide or hide signal is received.

According to a further embodiment, the invention provides a processor unit, comprising:

an interface that is constructed to receive a scrollable image stack from a tomography unit; and a processor device that is constructed to calculate an output for a display unit, wherein the output includes a primary image intended for representing the image stack that is received, and wherein the output includes a secondary image with additional information, wherein the secondary image is displayed overlaid on the primary image once an unhide or hide signal is received, and wherein the interface is further constructed to provide the calculated output.

According to a further embodiment, the invention provides an apparatus, comprising:

an interface, to receive a scrollable image stack from a tomography device; and at least one processor, to calculate an output for a display, the output including a primary image to represent the scrollable image stack received, and including a secondary image including additional information, and once an unhide or hide signal is received, the secondary image is displayed overlaiding the primary image, and wherein the interface is further constructed to provide the output calculated.

According to a further embodiment, the invention provides a system for better examination of tomographically imaged dynamic image stacks.

According to this, an embodiment of the invention provides a system for calculating an output from a tomographic scrollable image stack, including a large number of generated sectional images of a tissue to be examined, including:

a tomography device to provide the scrollable image stack to the interface;

a processor unit or apparatus according to at least one embodiment of the present invention; and a display to display the output calculated.

In the context of an embodiment of the present invention, the display unit includes a monitor, a display, a touch display or a display panel that communicates with the system and/or the components of the system by way of a communication connection. The communication connection can take the form of a DVI, HDMI, DisplayPort connector, USB or S-video/composite video and/or can be made over a network connection using streaming.

Further, an embodiment of the invention provides a computer program with program code for performing a method according to one of the preceding embodiments of the method when the computer program is executed on an electronic device. The computer program may be provided as a signal via download, or be stored in a memory unit of a portable device with computer-readable program code therein, in order to cause a system to execute instructions in accordance with the above-mentioned method. The fact that the invention is implemented as a computer program product has the advantage that already existing electronic devices such as computers or portable devices can easily be used as a result of software updates in order, as proposed by the invention, to enable an output from a tomographic scrollable image stack to be better calculated.

The computer program can be executed in a distributed manner, such that for example individual method steps are performed on a first processor unit and the other method steps are performed on a second processor unit.

BRIEF DESCRIPTION OF THE DRAWINGS

The present invention will be explained in more detail below with reference to the example embodiments that are indicated in the schematic figures of the drawings. In the drawings.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art.

Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Accordingly, and according to a first embodiment, the invention provides an in particular computer-implemented method for calculating an output from a tomographic scrollable image stack that includes a large number of generated sectional images of a tissue to be examined, comprising:

receiving a scrollable image stack from a tomography unit; and calculating the output for a display unit, wherein the output includes a primary image that is determined for representing the received image stack, and wherein the output includes a secondary image with additional information, wherein the secondary image is displayed overlaid on the primary image once an unhide or hide signal is received.

In the context of the present application, the term "image stack" should be understood to mean a calculated image of a transverse section through an object undergoing examination, for example the tissue that is to be examined. The transverse section includes a plurality of adjacent sections that represent different slices of the object undergoing examination. The sections represent, as a first-order approximation, the density prevailing in this region of the object undergoing examination. Thus, the image stack represents a number of slices of the object undergoing examination that are present on sorting.

Moreover, in the context of the present application, the term "scrollable image stack" should be understood to mean a two-dimensional representation of a plurality of axial slices, which can be viewed by scrolling through the plurality of axial slices, wherein scrolling can be performed in two mutually opposing directions and in each case a preceding or succeeding axial slice—depending on the direction of scrolling—causes a currently displayed axial slice to be displayed.

At least one embodiment of the present application is based on the realization that there is a need for better calculation of an output from a tomographic scrollable image stack, for example for the purpose of achieving better examination and/or diagnostic results with a lower error rate. Moreover, it is possible to leaf through the image stack more efficiently without any need to accept a loss of information (for example as a result of covering up image information).

Representation in methods of the prior art may result in the primary image being continuously overlaid by secondary information. When necessary, the viewer then has to explicitly hide this information and unhide it again. If the additional information is particularly useful when particular image components are to be located during leafing through the image stack, then according to the present invention the additional information can advantageously be unhidden precisely when it is required, and hidden precisely when display of the additional information is no longer required. In this case, there is no need for the viewer to unhide and hide images explicitly or manually.

Advantageously, annotations that have been calculated by a CAD method and are intended to draw attention to particular anomalies in the picture section can be output during leafing through the image stack, drawing the viewer's attention to a corresponding finding. Advantageously, when the display is static, or in a configuration with relatively slow leafing, only the primary image is represented in order not to impair a corresponding assessment by the viewer, for example a radiologist. Moreover, the viewer is provided with a reference between the additional information and the image stack or between the additional information and a sectional image of the image stack.

Advantageous embodiments and developments are apparent from the subclaims and from the description, which is given with reference to the figures.

The terms used in this application are explained in more detail below.

In an advantageous embodiment, the tomography unit is a magnetic resonance imaging tomography unit. A magnetic resonance imaging tomography unit is used to carry out magnetic resonance imaging (MRI). Magnetic resonance imaging is an imaging method that is used primarily in medical diagnostics to represent the structure and function of the tissue and/or organs of a human or animal body. MRI can be used to generate sectional images of the human or animal body that enable the tissue and organs, or changes in the organs as a result of disease, to be assessed. MRI is based on magnetic fields that are generated by a magnetic resonance imaging tomography system, and magnetic alternating fields in the high-frequency range by which particular nuclei of atoms in the body can be excited to resonance, as a result of which an electrical signal in the form of a voltage is emitted until the excitation has died away. Types of tissue differ in respect of their molecular structure, and this results in a difference in the electrical signal and a corresponding image or image stack.

In a further advantageous embodiment, the tomography unit is a computed tomography unit. Computed tomographs are based on the principle of X-ray radiation, in which a computer is used to generate sectional images calculated from the absorption values of X-ray signals passing through the body. The digital sectional images are generated from a computer-based evaluation of a large number of X-ray images of an object that are captured from different directions. The sectional images are provided in an image stack.

In a further advantageous embodiment, the unhide or hide signal is provided during leafing through the scrollable image stack. In the context of the present application, the term "leafing" should be understood to mean output of a succeeding or preceding sectional image of the scrollable image stack, such that each separate sectional image can be viewed. During leafing, a corresponding unhide signal is provided, as a result of which the secondary image with the additional information is displayed overlaid on the primary image. In particular, the unhide and hide signal can be provided for a preconfigurable quantity of sectional images, or even for each individual sectional image, and processed for the purpose of calculating an altered output (with the primary and the secondary image).

In a further advantageous embodiment, the unhide or hide signal is provided during zooming in or out of the primary image. Advantageously, the unhide or hide signal may be provided by zooming in or out of a picture section of the primary image. In this way, the output from the tissue for examination can be assessed without additional information overlaid on it.

In a further advantageous embodiment, the unhide or hide signal is provided during panning of the primary image. Advantageously, the additional information of the secondary image is displayed overlaid on the primary image, by panning the primary image. In this way, the output from the tissue for examination can be assessed without additional information overlaid on it.

In a further advantageous embodiment, the unhide or hide signal is provided in dependence on the speed of leafing, zooming in or out and/or panning. Advantageously, overlaying on the primary image can be adapted to the corresponding unhide and hide signals, and can enable a more sensitive response on overlaying the primary image with the secondary image. For example, in this way the primary image is not overlaid with the secondary image each time zooming in or out is performed, but only once a corresponding speed sensor has detected a certain and/or configured speed of zooming in or out.

In a further advantageous embodiment, the unhide or hide signal is provided in a multiplane reconstruction (MPR) during a change in the position of the current sectional image in space as a result of rotation or a change in curvature. Advantageously, the secondary image may be displayed overlaid on the first primary image if a change in the position of the current sectional image in space is detected that supports an assumption that further detailed information is desired, which is accordingly displayed.

In a further advantageous embodiment, a hide signal is provided automatically—and hence preferably without any further intervention by the user—for a configured duration after generation of the unhide signal (such as leafing). Advantageously, the overlaid secondary image can be hidden on the basis of a configurable hide period. For example, the hide period may be configured such that hiding in dynamic stages (fade out) is enabled, for example having the overlay grow paler until it becomes transparent, making a better comparison between the primary image and the secondary image possible. The hide period may be for example in a range of from 10 ms to 5 s, preferably in a range of from 20 ms to 2.5 s, particularly preferably in a range of from 20 ms to 1 s. The hide period can be configured by the viewer. At all other times, only the primary image information is shown.

In one embodiment, the hide period is configured automatically on the basis of the speed of leafing, zooming in or out, and/or panning.

In an alternative embodiment, the secondary image is displayed overlaid on the primary image until the hide period has elapsed. After the hide period has elapsed, the secondary image is hidden.

In a further advantageous embodiment, the primary image is unhidden in a windowing including a range of other CT values. Advantageously, this makes the anatomy more clearly recognizable at a glance.

In a further advantageous embodiment, the additional information includes at least landmarks. A landmark is an annotation that has the character of a clarification or explanation. A landmark indicates for example a particular point on a sectional image, in a combined view of a plurality of sectional images, or in an image stack, represented for example by crosses, dots, arrows, circles or labels, which may be identified rapidly and recognized quickly, manually or automatically, and which allow a plurality of sectional images to be mapped onto one another. Moreover, landmarks provide an item of information on position, and may contain a description for picking out certain regions. Landmarks may display individual locatable features in the image, for example anatomical structures or lesions. The landmarks may be provided with an identifier for the purpose of description.

In a further advantageous embodiment, the additional information includes at least contours. Contours can mark or delimit the borders of a particular volume in the image stack in relation to its environment, for example parts of organs, organs, organ systems, body parts, changes (in particular tumors), or implants. The contour of the volume may be used for example in a therapy planning system in order to make it possible to gauge the size of the dose, for example in radiation therapy, that this organ will receive during therapy. As an alternative, a contour can be used to precisely monitor a tumor and its size and/or changes, since the volume and/or border can be delineated precisely.

In an advantageous embodiment, the landmarks and contours can be stored in a storage unit and used as a reference and/or comparison for a further investigations. The storage unit includes for example a hard disk (HDD), random access memory (RAM), flash memory and/or an external storage device, for describing a portable data store.

In a further advantageous embodiment, the additional information includes at least identifier/classification information. The identifier/classification information can be used to mark recognized changes, for example marking whether a tumor is benign or malignant, for example by colored marks or text marks. The identifiers/classifications may be used for example for teaching neural networks, since these display a recognized change and provide a way of classifying this change. As a result of teaching the identifier/classification information to a neural network, it is possible to detect changes automatically. The identifier/classification information moreover provides additional information, as a result of being displayed overlaid on the primary image.

In a further advantageous embodiment, the additional information includes at least one further image stack produced from different types of reconstructions of the same captured data set and/or further captured data sets. Reconstructions may be differentiated here in particular by artifact correction methods (radiation curing correction and/or metal artifact correction) and/or reconstruction kernels and/or regularization parameters. Advantageously, within the reconstruction it is possible to influence the resulting image definition. For example, it is possible to select reconstructing an image with as high-definition an image as possible, although this can simultaneously result in a high level of noise in the image. As an alternative, an image with low noise can be requested because small differences in density are to be examined. Advantageously, in the context of the reconstruction it is possible to influence how the resulting image is to be influenced, as a result of which images for the corresponding purpose and use can be provided. For example, for an assessment of soft tissue, a relatively low-definition but noise-free image may be advantageous, whereas when hairline fractures in bones or bone crests are to be assessed, a high-definition reconstruction is advantageous.

Using the artifact correction methods, artifacts caused by implants (metal) in the individual sectional images of the image stack can be eliminated. However, artifact correction methods have the disadvantage that any pathological structures are also "corrected away" (and so removed) by the correction, so they cannot then be assessed. Advantageously, an image stack without artifact correction methods can be displayed in a primary image and an image stack with artifact correction methods can be displayed, overlaid thereon, in a secondary image, as a result of which any pathological structures can be better identified. Verification of the information represented is simplified.

In a further advantageous embodiment, the additional information includes at least one further image stack that results from post-processing the primary image and/or other images. Advantageously, the additional information may include further image stacks that are post-processed for example by image filters (noise suppression, emphasis of edges) or point transformation (e.g. equalization or alignment of histograms). Advantageously, post-processing may also result in annotations (landmarks, contours, text marks). These can be transferred in an image stack that contains these annotations as raster graphics, with the display regions that do not contain any annotation graphic elements being kept completely transparent. In an alternative embodiment, it is possible to input the image values of an image stack that was originally sent for post-processing or an image value that results from combining the original image stacks, with the result that the annotation graphic elements overwrite or are overlaid on this transferred image value.

In a further advantageous embodiment, a hide signal is provided for the additional information that is continuously overlaid on the primary image during leafing through the image stack. The secondary image with the additional information is continuously displayed overlaid on the primary image, and during leafing a hide signal is provided by means of which the secondary image is hidden.

In a further advantageous embodiment, the overlaid form includes overlaying on the grayscale values of the primary image the grayscale values of the secondary image, by blending the grayscale values. In particular, blending the grayscale values can enable the secondary image to partly or entirely overlay the primary image contents (the displayed content of the primary image). Advantageously, the primary image and the secondary image may be represented as a primary grayscale image and a secondary grayscale image from which the color values are screened out. Ultimately, the grayscale images merely represent a one-dimensional form of the images, since a CT is only able to determine the efficient attenuation coefficient, and additional, more detailed calculations and hence more processing power are required for colored representation.

In one embodiment, for the primary grayscale image there may be used an image to which no artifact corrections have been made, and the image that has been reconstructed with artifact corrections may be used for the secondary image with additional information. During scrolling, the image without artifacts may for example be displayed. Once the image is no longer being scrolled through, the image is represented with the artifacts. In this way, advantageously, the differences between the first and the second grayscale image become clear.

In a further advantageous embodiment, the blend of grayscale values is based on a configured value and is configurable invariably, in particular during leafing or, depending on the leafing speed, is configurable variably. In this way, the blend may be characterized in accordance with a preference of the viewer. In the case of more rapid leafing, the additional information is for example displayed all the more strongly until a point is reached at which the additional information completely overlays the primary image content above a certain leafing speed. After leafing ends, the blend of grayscale values may be maintained for a finite period by the image stack in the condition of the blend during leafing.

In an alternative embodiment, the grayscale values of the secondary image with the additional information can be continuously hidden until the hide period comes to an end. The duration of the hide period and the hiding behavior can in this case be directly or indirectly influenced by the leafing procedure.

In a further advantageous embodiment, the grayscale values are blended by a linear combination including a first coefficient and a second coefficient that determine the proportion of the primary image and the secondary image. Advantageously, it is thus possible to calculate the grayscale value of the primary image or the secondary image that is represented. The first coefficient describes the proportion of the primary image, and the second coefficient describes the proportion of the secondary image with the additional information in the blend of grayscale values. In particular when there is a complete overlay by the secondary image with the additional information, the value of the first coefficient is zero. During periods in which only the primary image is displayed, the value of the first coefficient is equal to one and that of the second coefficient is equal to zero. In particular a weighted sum of grayscale values is formed, with the grayscale images of the primary and secondary images being represented as vectors. The primary grayscale image corresponds to the vector 1 and the secondary grayscale image to the vector 2. Blending is performed by linearly combining the vectors. In this case, the vector 1 is multiplied by a scalar factor, and the vector 2 is multiplied by a further scalar factor. The blended grayscale image is thus produced from the sum of the two scaled vectors. Advantageously, it is thus possible, from two grayscale images, to display an image including grayscale values that makes it possible to dynamically blend the grayscale values.

In a further embodiment, a blend that does not vary over time can be achieved in that the first and the second coefficient are selected in a manner that is invariable over time in the display space during leafing through the image stack. The coefficients may be established for example by the viewer.

In a further embodiment, the blend may be formed in dependence on the speed, for example the scrolling speed. Here, the coefficients are also made speed-dependent.

In a further embodiment, the secondary image may be hidden continuously. Here, taking as a starting point the coefficient that was selected last—during leafing—it may be assumed for example that the hide period adopts a linear course, in which the first coefficient again adopts the value one and the second coefficient again adopts the value zero.

In a further embodiment, the hide period may be determined by a mathematical function, for example a power function, a polynomial, an exponential function, a trigonometric function, and combinations and the inverse thereof. In particular, there should be a constant transition (and where possible also a constantly differentiable transition) between the last condition selected during the period of leafing and the hide period, and between the hide period and the period during which only the primary image is then displayed.

In one embodiment, the linear combination may be performed by an affine combination in which the sum of the coefficients must be one at any given point in time. However, this does not rule out the possibility that a coefficient has a negative value. In a further embodiment, the linear combination may be performed by a convex combination. The convex combination represents an affine combination with the additional condition that all the coefficients are greater than or equal to zero. This has the advantage that further grayscale images or grayscale image variants can be incorporated into the blend.

In a further advantageous embodiment, the overlaid form includes overlaying values from the color spectrum or a value for transparency on the grayscale values. Grayscale values of a grayscale image here represent a one-dimensional subset within the range of color values, and can thus advantageously be combined with color value images. The transparency information makes this possible in that the additional information is not overlaid in the entire image range. Typically, a color value is represented for example by a vector having three individual components. Each of these three individual components is associated with one of the primary colors (red, green, blue) and defines the brightness of the primary color in the blend. It is thus possible for a blend of the three colors to cover the entire color spectrum. Without any transparency, the blend of primary image and additional image or secondary image can likewise take the form of a linear combination of image value vectors using a first and a second coefficient, by analogy with the embodiments for blending grayscale images. In a further embodiment, an additional transparent value may be associated with each image value in the primary image and the secondary image. The transparency value has for example a value greater than or equal to zero and less than or equal to one. In a blend, this transparency value has to be combined with the respectively first or second coefficient, for example by multiplication and subsequent renormalization in order to keep the sum of the resulting effective coefficients to one, in order for example to achieve an affine combination.

In a further embodiment, the additional information to be overlaid is calculated in the form of an image value to be overlaid during the leafing procedure, from the image values of the primary image and/or image values of the primary image that were displayed and/or overlaid at previous points in time. The image value to be overlaid may be blended with the image values of the primary image, in a manner corresponding to the variants described in the embodiments above, for example by way of a linear combination or a variant of the linear combination. Calculation of the image value to be overlaid may be varied depending on the leafing speed in respect of the procedure and parameterization. The superimposed image value may for example be a linear combination of the current image value and a number of the previously calculated image values. Moreover, the coefficients of the linear combination may be affected by the leafing speed.

In a further embodiment, the secondary image with the additional information, which is continuously displayed in overlaid form, may be hidden during leafing through the image stack. In this respect, a coefficient that controls the overlaying of this additional information that is to be hidden must have a value equal to zero during leafing and a value that is not equal to zero when the display is static. Advantageously, the embodiment can be combined with being unhidden during leafing.

In a further embodiment, the primary and secondary image may be blended in accordance with the resulting brightness or color values intended for display. This has the advantage that the primary image is unhidden, as additional information, but has different windowing. Windowing establishes which portion of the scale of measured density values in the image is allocated grayscale values from black to white. In this way, the image contrast of the tissue to be assessed is optimized. Windowing is also applied to the representation of signal intensities. The underlying rationale for this is that the values stored in an image stack do not always correspond directly to an image value or brightness value intended for display. Here, these values must be converted to a brightness value. For example, the attenuation information in the image stack is stored in Hounsfield units (HU). On windowing, an interval on the HU scale is selected, and values below the lower limit or above the upper limit are associated with the corresponding limit. The value interval is then mapped for example onto a linearly rising brightness interval or a grayscale interval. As an alternative, this value interval may be mapped onto a variable-brightness color interval or any desired color scale. As an alternative, for example the values stored in the same scale—for example two image stacks in the HU scale—can be blended accordingly and consequently mapped onto one brightness scale.

In an alternative embodiment, only one primary image is displayed, while leafing provides another parameterization of the representation. In this context, parameterization can be performed continuously at the start of leafing and once leafing has ended. For example, during static display, it may be useful to select windowing that is specifically matched to the region of the tissue and the corresponding task. For this purpose, this windowing may be restricted in particular to a comparatively small measurement value interval for display (for example, in the case of X-ray CT, to a small HU interval). In that case, the windowing is as it were a mapping of the measurement value interval for display onto the image value interval. Advantageously, in this way small contrasts in soft tissue can be represented. Further, during leafing a relatively large measurement value interval (e.g. in particular HU interval) is mapped in order to allow the anatomy to be represented more clearly when viewed at a glance. Moreover, the breadth of the measurement value interval may be dependent on the leafing speed. For example, the greater the leafing speed, the broader the interval becomes.

Up to this point, the embodiments been described in terms of embodiments of the method. Features, advantages or alternative embodiments may be associated with the other claimed subject-matter (e.g. the processor unit, the system or a computer program product) and vice versa. In other words, the subject-matter that is claimed or described in relation to the processor unit may be improved by features that are described or claimed in the context of the method, and vice versa. In this case, the function features of the method are embodied by structural units of the processor unit or the system, and vice versa. In general in information technology, a software implementation and a corresponding hardware implementation are equivalent. Thus, for example a method step may be performed in order to "store" data using a storage unit and corresponding instructions for writing data to the memory or store. In order to avoid redundancy, although the processor unit may also be used in the alternative embodiments described with reference to the method, these embodiments are not explicitly described again in relation to the processor unit.

According to a further embodiment, the invention provides a processor unit, comprising:

an interface that is constructed to receive a scrollable image stack from a tomography unit; and a processor device that is constructed to calculate an output for a display unit, wherein the output includes a primary image intended for representing the image stack that is received, and wherein the output includes a secondary image with additional information, wherein the secondary image is displayed overlaid on the primary image once an unhide or hide signal is received, and wherein the interface is further constructed to provide the calculated output.

The processor unit for performing the above-mentioned classification task may take the form of a computer, personal computer, or workstation in a computer network, and may comprise a processing device (processor or processors), a system memory and a system bus that couples different system components, including the system memory, to the processing device. The system bus may be one of a plurality of types of bus structure, including a memory bus or a memory controller, a peripheral bus and a local bus, using any desired number of bus architectures.

The system memory may comprise a read-only memory (ROM) and/or a random access memory (RAM). A basic input/output system (BIOS) which contains basic routines that help to transfer information between elements of the PC, for example on starting up, may be stored in the ROM. The processor unit may also contain a hard disk drive for reading from and writing to a hard disk, a magnetic disk drive for reading from or writing to a (for example removable) magnetic disk, and an optical disk drive for reading from or writing to a removable (magnetic) optical disk such as a compact disk or other (magnetic) optical media. The hard disk drive, the magnetic disk drive and the (magnetic) optical drive may be coupled to the system bus by way of a hard disk interface, a magnetic disk drive interface and a (magnetic) optical drive interface. The drives and the associated storage media allow non-volatile storage of machine-readable instructions, data structures, program modules and other data for the computer.

Although the example environment described here makes use of a hard disk, a removable magnetic disk and a removable (magnetic) optical disk, those skilled in the art will realize that other types of storage media such as magnetic cassettes, flash memory cards, digital video disks, Bernoulli boxes, "Random Access Memories" (RAMs), "Read Only Memories" (ROMs) and similar can be used instead of or in addition to the storage devices enumerated above. A plurality of program modules, such as an operating system, one or more application programs, such as the method for calculating an output and/or other program modules and/or program data, can be stored on the hard disk, magnetic disk, (magnetic) optical disk, ROM or RAM.

A user may input commands and information to the computer using input devices such as a keyboard and a pointing device. Other input devices, such as a microphone, joystick, gaming pad, satellite dish, scanner or similar, may likewise be included. These and other input devices are often connected to the processing device by way of a serial interface coupled to the system bus. However, it is also possible for input devices to be connected by way of other interfaces, such as a parallel interface, a game interface or a universal serial bus (USB). A monitor (such as a GUI) or another type of display device may also be connected up to the system bus by way of an interface such as a video adapter. In addition to the monitor, the computer may also comprise other peripheral output devices such as speakers and printers.

The processor unit can be operated in a network environment that defines logical connections with one or more remote computers. The remote computer may be another personal computer, a server, a router, a networked PC, a peer device or another common network node, and may comprise many or all of the elements described above in relation to the personal computer. Logical connections include a local area network (LAN), a wide area network (WAN), an Intranet and the Internet.

Further, the processor unit may take the form of a system-on-a-ship design on a microcontroller or programmable chip, for example an ASSIC or FPGA.

According to a further embodiment, the invention provides a system for better examination of tomographically imaged dynamic image stacks.

According to this, an embodiment of the invention provides a system for calculating an output from a tomographic scrollable image stack, including a large number of generated sectional images of a tissue to be examined, including:

a tomography unit constructed to provide a scrollable image stack;

a processor unit according to at least one embodiment of the present invention; and a display unit constructed to show the calculated output.

In the context of an embodiment of the present invention, the display unit includes a monitor, a display, a touch display or a display panel that communicates with the system and/or the components of the system by way of a communication connection. The communication connection can take the form of a DVI, HDMI, DisplayPort connector, USB or S-video/composite video and/or can be made over a network connection using streaming.

Further, an embodiment of the invention provides a computer program with program code for performing a method according to one of the preceding embodiments of the method when the computer program is executed on an electronic device. The computer program may be provided as a signal via download, or be stored in a memory unit of a portable device with computer-readable program code therein, in order to cause a system to execute instructions in accordance with the above-mentioned method. The fact that the invention is implemented as a computer program product has the advantage that already existing electronic devices such as computers or portable devices can easily be used as a result of software updates in order, as proposed by the invention, to enable an output from a tomographic scrollable image stack to be better calculated.

The computer program can be executed in a distributed manner, such that for example individual method steps are performed on a first processor unit and the other method steps are performed on a second processor unit.

The embodiments and developments above can be combined with one another in any desired manner where this is practical. Further possible embodiments, developments and implementations of the invention also include combinations that are not explicitly mentioned, of features of the invention that are described above or below in relation to example embodiments. In particular here, those skilled in the art will also add individual embodiments to improve or supplement the respective basic form of the present invention.

The attached drawings are intended to further elucidate the embodiments of the invention. They illustrate embodiments and serve in conjunction with the description to clarify the principles and concepts of the invention. Other embodiments, and many of the advantages mentioned, will be apparent from the drawings. The elements of the drawings are not necessarily shown on the same scale as one another.

In the figures of the drawing, elements, features and components that are alike, functionally equivalent and have the same effect are each provided with the same reference numerals unless otherwise indicated.

Figure 1:
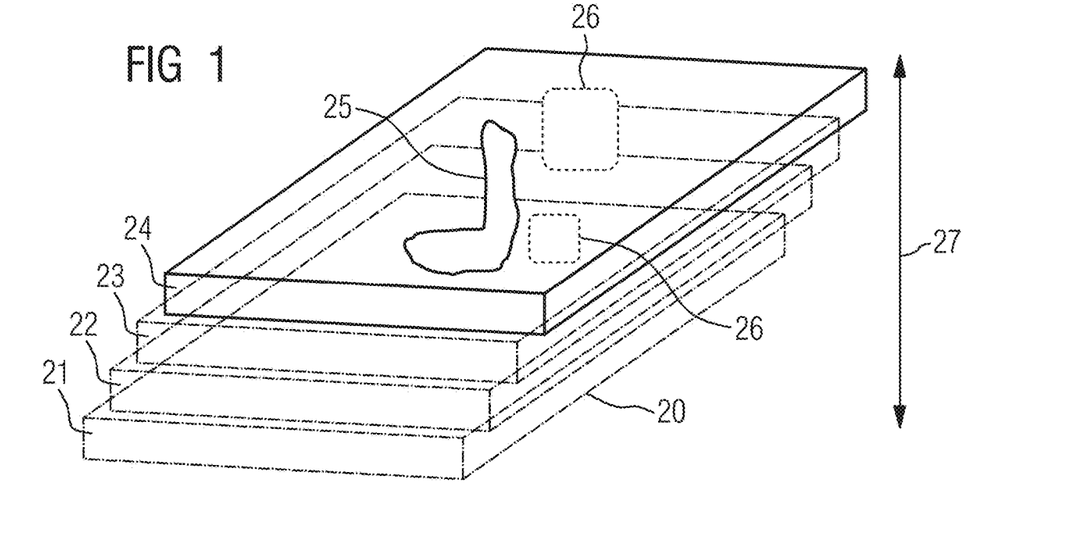
FIG. 1 shows a block diagram for representing a calculated output from a tomographic scrollable image stack.
Figure 4:
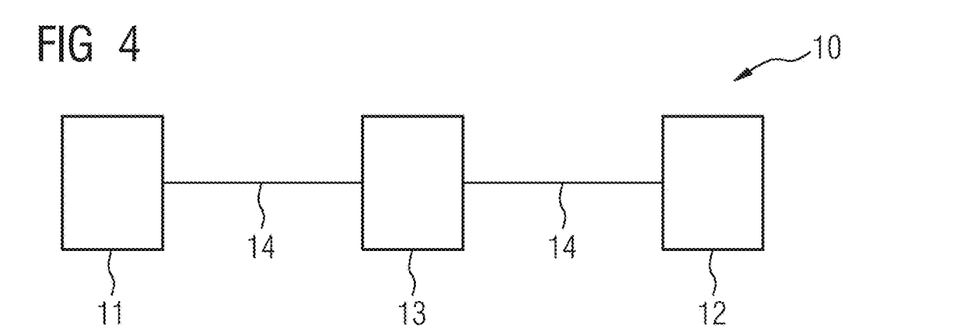
FIG. 4 shows a block diagram for representing an example embodiment of a system according to the invention.

FIG. 1 shows a block diagram for representing a calculated output from a scrollable image stack 20 provided by a tomography unit 11 (see FIG. 4). The tomography unit 11 may take the form of a magnetic resonance imaging tomography unit or a computed tomography unit. Further technical embodiments, modifications and technical innovations for tomographs that provide images in an image stack 20 for analysis are applicable to embodiments of the present invention.

An image stack 20 represents a calculated image of a transverse section through an object undergoing examination, for example the tissue 25 to be examined. The transverse section includes a plurality of adjacent sections or sectional images 21, 22, 23, 24 that represent different slices of the object undergoing examination. The sectional images 21, 22, 23, 24 represent, as a first-order approximation, the density prevailing in this region of the object undergoing examination. Thus, the image stack 20 represents a number of slices of the object undergoing examination that are present on sorting.

The sectional image 24 represents for example the active or currently displayed sectional image of the image stack 20 that is viewed by a viewer such as a radiologist for the purpose of diagnosis. Represented in the sectional image 24 is a slice of the tissue 25 for examination. The term "a tissue 25 for examination" should be understood to mean the tissue of a human or animal body, or organs of a human or animal body. Moreover, in the sectional image 24 additional information 26 is represented in a secondary image. The secondary image with the additional information 26 may, after an unhide or hide signal 27 has been received, be displayed overlaid on the primary image with the image stack 20 including the sectional images 21, 22, 23, 24.

In one embodiment, the additional information 26 includes annotations. The annotations include for example landmarks, contours and/or identifier/classification information. In a further embodiment, the additional information 26 includes a further image stack 20, which results from different types of reconstruction of the same captured data set and/or further captured data sets. In a further embodiment, the additional information 20 includes image stacks that result from a post-processing of the primary image and/or other images.

According to an embodiment of the present invention, an output is calculated for a display unit 12 (see FIG. 4). The output includes a primary image that is intended for representing the received image stack 20. Furthermore, the output includes a secondary image with additional information 26, wherein the secondary image is displayed overlaid on the primary image once an unhide or hide signal 27 is received. The unhide or hide signal 27 is provided by the processor unit 13 on the basis of an input signal from the viewer. The input signal may include scrolling, leafing, zooming in, zooming out, panning, rotating and/or subjecting to a curve.

In one embodiment, the unhide or hide signal 27 may be performed by scrolling or leafing through the individual sectional images 21, 22, 23, 24 in the image stack 20. As a result of scrolling or leafing, the preceding or successive sectional image is actively shown, depending on the direction of scrolling or leafing. During scrolling or leafing, the additional information 26 is displayed overlaid on the primary image. In one embodiment, the unhide or hide signal 27 can be generated by zooming in or out or panning the picture section, or by rotating and/or changing the curvature of the sectional image 21, 22, 23, 24 in an MPR. In one embodiment, the additional information 26 continues to be displayed overlaid on the primary image while the unhide or hide signal 27 is provided. Once the unhide or hide signal 27 is no longer available, the additional information is hidden. In one embodiment, the additional information can be hidden dynamically within a configurable hide period. In a further embodiment, the duration of hiding is determined by the speed of the direction of scrolling or leafing or by the further input signals.

In a further embodiment, the overlaid form includes overlaying the grayscale values of the primary image, including the image stack 20, with the grayscale values of a secondary image including the additional information 26. In the overlaid form, the grayscale values of the primary image may be covered up, at least partly or entirely, by the grayscale values of the secondary image. Overlaying is performed by blending the grayscale values. In one embodiment, the blending is invariable and characterized in accordance with a preference of the viewer. In an alternative embodiment, the blending is configurable. The blending may for example be configured by scrolling or leafing through the image stack 20, by zooming in or out of the picture section, or by panning a picture section.

In a further embodiment, the blending may be configured by the speed of scrolling or leafing through the image stack 20, the speed of zooming in or out of the picture section, or the speed of panning a picture section. Blending of the grayscale values may be maintained after the end of scrolling or leafing through the image stack 20, or by the further input signals for a configurable period, and then hidden. In an alternative embodiment, blending of the grayscale values may be hidden dynamically over a configurable period. The period may be configured by way of the speed of the input signals.

In one embodiment, the blending of grayscale values may take place through a linear combination in which a first coefficient determines the proportion of the primary image and a second coefficient determines the proportion of the secondary image. The linear combination may take the form of an affine combination or be performed by a convex combination.

In a further embodiment, the image values may also adopt values from the color spectrum, including transparency. This has the advantage that, for example in order to display a contour of a lung, the corresponding values of the primary image can be overlaid, and thus findings relating to ventilation become visible at the corresponding locations on the lung and for example the volume of certain regions of the lung during inspiration and expiration can be determined.

In an alternative embodiment, the secondary image with the additional information 26 can be displayed continuously and hidden by the unhide and hide signal 27, in particular by a hide signal. The hide signal is provided on the basis of the input signal.

Figure 2:
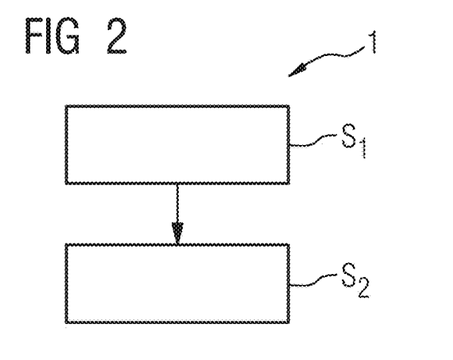
FIG. 2 shows a flow chart for representing a possible example embodiment of a method according to the invention.

FIG. 2 shows a flow chart for representing a possible example embodiment of a method according to the invention.

In the example embodiment illustrated, the method 1 includes a plurality of steps. In a first step S1, a scrollable image stack 20 (see FIG. 1) is received from a tomography unit 11 (se FIG. 4).

In a second step S2, the output for a display unit 12 (see FIG. 4) is calculated, wherein the output includes a primary image that is intended for representing the received image stack 20, and the output includes a secondary image with additional information 26, wherein the secondary image is displayed overlaid on the primary image once an unhide or hide signal 27 (see FIG. 1) is received. The secondary image can be displayed overlaid on the primary image on a display unit 12.

Figure 3:
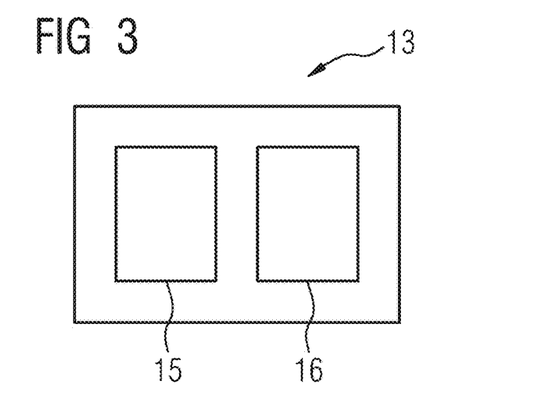
FIG. 3 shows a block diagram for representing a possible example embodiment of a processor unit according to the invention.

FIG. 3 shows a block diagram for representing a possible example embodiment of a processor unit according to the invention.

In FIG. 3, the reference numeral 13 designates a processor unit. The processor unit 13 includes a communication interface 15 and a processing device 16. The processor unit 13 may, as stated above, take the form of a computer, personal computer, workstation, server or computer in a server network (cloud) that communicate over a communication network, for example a local network or the Internet.

The communication interface 14 is constructed to receive a scrollable image stack 20 from a tomography unit, and to provide the output calculated by the processing device 15, for example to a display unit 12 (see FIG. 4).

The processing device 16 is constructed to calculate an output for a display unit 12, wherein the output includes a primary image that is intended for representing the received image stack 20 (see FIG. 1), and the output includes a secondary image with additional information 26 (see FIG. 1), wherein the secondary image is displayed overlaid on the primary image once an unhide or hide signal 27 is received.

FIG. 4 shows a block diagram for representing an example embodiment of a system according to the invention.

In FIG. 4, reference numeral 10 designates the system according to the invention for calculating an output from a tomographic scrollable image stack. The system 10 includes a tomography unit 11, for example a magnetic resonance imaging tomography unit or a computed tomography unit, and a processor unit 13 for calculating an output from a primary image for representing the received image stack 20, wherein this output is displayed, overlaid with a secondary image with additional information 26, on a display device 12. The components (tomography unit 11, processor unit 13, display unit 12) of the system 10 communicate with one another by way of a communication connection 14. The system 10 may take the form of a distributed system 10, in which the components are positioned at distributed locations and are connected to and communicate with one another by way of the communication connection 14, for example a local network (LAN) or a global network (MAN, WAN). In an alternative embodiment, the components may be positioned highly centrally in relation to one another and communicate by way of serial or parallel communication connections or communication interfaces (Ethernet, USB, FireWire, CAN-BUS, RS-485).

To summarize, embodiments of the present invention relates to a method and a system for calculating an output from a tomographic scrollable image stack, including a large number of generated sectional images of a tissue to be examined. In this context, a tomographic scrollable image stack is received. An output for a display unit is calculated, wherein the output includes a primary image that is intended for representing the received image stack, and wherein the output includes a secondary image with additional information, wherein the secondary image is displayed overlaid on the primary image once an unhide or hide signal is received.

In this context, a reference may be provided between the additional information of the secondary image and the slice of tissue for examination that is shown in the sectional image of the image stack.

Where it has not yet explicitly been set out, although useful and in the spirit of the invention, individual example embodiments, individual sub-aspects or features thereof can be combined or exchanged with one another without departing from the scope of the present invention. Advantages of the invention described in relation to an example embodiment also apply without explicit mention, where transferable, to other example embodiments.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for calculating an output from a tomographic scrollable image stack, including a large number of generated sectional images of a tissue to be examined, the method comprising:
    receiving the tomographic scrollable image stack from a tomography device; and
    calculating the output for a display, the output including a primary image, to represent the tomographic scrollable image stack received, and including a secondary image including additional information, the secondary image being displayed overlaid on the primary image once an unhide signal or a hide signal is received,
    wherein the additional information includes at least one of:
        landmarks,
        contours,
        identifiers,
        classification information,
        an image stack, produced from different types of reconstruction of at least one of a same captured data set and further captured data sets, and
        an image stack resulting from post-processing of least one of the primary image and other images.

2. The method of claim 1, wherein the tomography device is a magnetic resonance imaging tomography unit or a computed tomography unit.

3. The method of claim 1, wherein the unhide signal or the hide signal is received during a leafing through of the tomographic scrollable image stack.

4. The method of claim 1, wherein the unhide signal or the hide signal is received during a zooming in or out of the primary image.

5. The method of claim 1, wherein the unhide signal or the hide signal is received during a panning of the primary image.

6. The method of claim 1, wherein the unhide signal or the hide signal is received in a multiplane reconstruction during a change in position of a current sectional image in space, as a result of rotation or a change in curvature.

7. The method of claim 1, wherein the hide signal is provided automatically and received for a configured duration, after generation of the unhide signal.

8. The method of claim 1, wherein a hide signal is provided for the additional information that is continuously overlaid on the primary image during leafing through the tomographic scrollable image stack.

9. A method for calculating an output from a tomographic scrollable image stack, including a large number of generated sectional images of a tissue to be examined, the method comprising:
    receiving the tomographic scrollable image stack from a tomography device; and
    calculating the output for a display, the output including a primary image, to represent the tomographic scrollable image stack received, and including a secondary image including additional information, the secondary image being displayed overlaid on the primary image once an unhide signal or a hide signal is received, wherein the secondary image displayed overlaid on the primary image includes overlaying, on grayscale values of the primary image, grayscale values of the secondary image, by blending the grayscale values of the primary image and the grayscale values of the secondary image.

10. The method of claim 9, wherein the blending of the grayscale values of the primary image and the grayscale values of the secondary image is based on a configured value or, depending on a leafing speed of leafing through the tomographic scrollable image stack, is configurable variably.

11. The method of claim 9, wherein the blending of the grayscale values of the primary image and the grayscale values of the secondary image includes blending by a linear combination including a first coefficient and a second coefficient, determining a proportion of the primary image and the secondary image.

12. The method of claim 9, wherein the secondary image being displayed overlaid on the primary image includes overlaying values from a color spectrum or a value for transparency on grayscale values.

13. A processor unit, comprising
a communication interface, to receive a scrollable image stack; and
a processing device, to calculate an output for a display, the output including a primary image, to represent the scrollable image stack received, and including a secondary image including additional information, and once an unhide or hide signal is received, the secondary image is displayed overlaying the primary image, and
the communication interface being further constructed to provide the output calculated, wherein the additional information includes at least one of:
landmarks,
contours,
identifiers,
classification information,
an image stack, produced from different types of reconstruction of at least one of a same captured data set and further captured data sets, and
an image stack resulting from post-processing of least one of the primary image and other images.

14. A system for calculating an output from a tomographic scrollable image stack, including a large number of generated sectional images of a tissue to be examined, including:
a tomography device, to provide the tomographic scrollable image stack;
the processor unit of claim 13 including the communication interface to receive the tomographic scrollable image stack as the scrollable image stack; and
a display unit, to show the output calculated.

15. A non-transitory computer program product storing program code for performing the method of claim 1 when the program code is executed on an electronic device.

16. An apparatus, comprising:
an interface, to receive a scrollable image stack from a tomography device; and
at least one processor, to calculate an output for a display, the output including a primary image to represent the scrollable image stack received, and including a secondary image including additional information, and once an unhide or hide signal is received, the secondary image is displayed overlaying the primary image, and
wherein the interface is further constructed to provide the output calculated,
wherein the secondary image displayed overlaid on the primary image includes overlaying, on grayscale values of the primary image, grayscale values of the secondary image, by blending the grayscale values of the primary image and the grayscale values of the secondary image.

17. A system, comprising:
a tomography device, to provide the scrollable image stack to the interface;
the apparatus of claim 16; and
the display to display the output calculated.

18. The method of claim 10, wherein the blending of the grayscale values of the primary image and the grayscale values of the secondary image includes blending by a linear combination including a first coefficient and a second coefficient, determining a proportion of the primary image and the secondary image.

19. The method of claim 1, wherein the secondary image displayed overlaid on the primary image includes overlaying, on grayscale values of the primary image, grayscale values of the secondary image, by blending the grayscale values of the primary image and the grayscale values of the secondary image.

20. The method of claim 19, wherein the blending of the grayscale values of the primary image and the grayscale values of the secondary image is based on a configured value or, depending on a leafing speed of leafing through the tomographic scrollable image stack, is configurable variably.

21. The method of claim 19, wherein the blending of the grayscale values of the primary image and the grayscale values of the secondary image includes blending by a linear combination including a first coefficient and a second coefficient, determining a proportion of the primary image and the secondary image.

22. A non-transitory computer program product storing program code for performing the method of claim 9 when the program code is executed on an electronic device.

23. The processor unit of claim 13, wherein the scrollable image stack is received from a tomography unit.

24. The system of claim 14, wherein the tomography device is a magnetic resonance imaging tomography unit or a computed tomography unit.

25. The system of claim 17, wherein the tomography device is a magnetic resonance imaging tomography unit or a computed tomography unit.

26. The processor unit of claim 13, wherein the secondary image displayed overlaid on the primary image includes overlaying, on grayscale values of the primary image, grayscale values of the secondary image, by blending the grayscale values of the primary image and the grayscale values of the secondary image.

* * * * *